United States Patent [19]

Sharkany et al.

[11] Patent Number: 4,619,391
[45] Date of Patent: Oct. 28, 1986

[54] SURGICAL STAPLING INSTRUMENT

[75] Inventors: Edward J. Sharkany, Huntington; Richard J. Mathews, Sr., Stratford, both of Conn.

[73] Assignee: Acme United Corporation, Fairfield, Conn.

[21] Appl. No.: 601,574

[22] Filed: Apr. 18, 1984

[51] Int. Cl.$^4$ ............................................. A61B 17/00
[52] U.S. Cl. .................................. 227/19; 128/334 R; 227/DIG. 1; 227/83
[58] Field of Search ............. 228/334 R; 227/DIG. 1, 227/19, 83

[56] References Cited

U.S. PATENT DOCUMENTS

4,411,378 10/1983 Warman .............................. 227/19

Primary Examiner—Paul A. Bell
Attorney, Agent, or Firm—Mattern, Ware, Stoltz & Fressola

[57] ABSTRACT

A unique, surgical stapling instrument is attained by incorporating staple guiding and supporting cam means positioned in active, cooperating relationship to the legs of the staple during its formation. In this way, unwanted angular pitching or wobbling of the staple during formation is substantially eliminated. In the preferred embodiment, staple tip positioning means are also provided in cooperative association with the staple being formed to assure controlled movement of the staple into the desired forming orientation, thereby substantially preventing jamming or double staple formation. In addition, the staple forming plate incorporates a unique construction which assures complete staple formation prior to exiting through the cooperating housing portal, while also providing a staple tip entry zone, allowing the tips of the next staple to be formed to be positioned in the desired plane prior to the crown portion thereof. The surgical stapling instrument of the present invention also preferably incorporates two independent handle portions, one of which is slidingly, interlockingly engaged with the housing of the stapling instrument in order to assure a securely interlocked surgical stapling instrument, while also allowing the housing to be formed of transparent material.

22 Claims, 23 Drawing Figures

SURGICAL STAPLING INSTRUMENT

TECHNICAL FIELD

This invention relates to surgical stapling instruments and, more particularly, to disposable surgical stapling instruments for closing wounds in skin and fascia tissue.

BACKGROUND ART

During the last several years, much effort has been expended in developing improved surgical stapling instruments. However, in spite of the extensive effort that has been expended in an attempt to improve the quality and consistent repeatability of surgical stapling instruments, in general, and disposable surgical stapling instruments in particular, this effort has failed to satisfy all of the industry demands. In particular, prior art surgical skin stapling instruments are generally incapable of providing consistent, repeatable results, or limiting staple jamming during use to inconsequential occurrence.

Furthermore, prior art surgical stapling instruments typically have been unable to achieve a disposable surgical stapling instrument which is competitively priced and is able to assure complete staple control during the formation of the staple for implanting the surgical staple in the skin or fascia of the patient. In addition, these prior art disposable surgical staplers have not been able to meet the requirements for comfort and ease of use for the widely diverse applications to which a surgical stapler is exposed.

Finally, prior art surgical stapling instruments have suffered from the inability to be capable of assembly ease, with a minimum of separate, independent components. Typically, many small parts have been required in most prior art surgical staplers which require extensive manufacturing equipment or time-consuming hand assembly steps.

Consequently, it is a principal object of the present invention to provide a surgical stapling instrument capable of controllably guiding the staple to be formed to the correct position for formation, as well as securely holding the staple during the formation process to prevent unwanted movement or rotation thereof.

Another object of the present invention is to provide a surgical stapling instrument having the characteristic features defined above which provide substantial complete jam-free operation.

Another object of the present invention is to provide a surgical stapling instrument having the characteristic features defined above which incorporate a minimum of component parts and is capable of rapid assembly.

A further object of the present invention is to provide a surgical stapling instrument having the characteristic features defined above which also incorporate staple holding and guiding means for securing the staple to be formed in the desired plane of formation.

Another object of the present invention is to provide a surgical stapling instrument having the characteristic features defined above which is capable of being comfortably held, gripped and used without difficulty by substantially all individuals.

Other and more specific objects will in part be obvious and will in part appear hereinafter.

SUMMARY OF THE INVENTION

The present invention overcomes the problems and difficulties encountered with prior art surgical stapling instruments by incorporating a uniquely constructed staple supporting channel member, and cooperating staple forming plate, as well as a unique interlocking assembly system. By employing the unique staple supporting channel member and staple forming plate of the present invention, all of the prior art problems encountered during the formation of the staple are completely eliminated. Instead, complete control over the staple during the forming process is attained, and undesirable and unwanted shifting, pivoting or wobbling movement of the staple during the forming process, typically encountered with prior art instruments, is eliminated.

In achieving these goals, the staple supporting channel member of the present invention incorporates staple guiding and camming means positioned for continuous cooperating control of each staple during the entire forming process. The staple guiding and camming means assures that each staple is moved from its particular position into the desired position for proper forming or clenching. In addition, the staple guiding and camming means cooperates with each staple during the forming process to assure controlled movement of the staple in the desired forming plane, preventing unwanted pivoting or wobbling of the staple. In this way, the staple supporting channel member of the present invention achieves complete staple control during the forming or clenching process each and every time the staple is formed.

The surgical stapling instrument of the present invention employs a minimum of component parts, all of which are designed for rapid and efficient assembly, achieving the surgical stapling instrument which can be manufactured at competitive prices for meeting the requirements inherent for a disposable surgical instrument. In this regard, the surgical stapling instrument of the present invention incorporates a housing which is formed from two mating halves in which is mounted a staple supporting channel member, along with its associated staples and spring loaded staple pusher. In addition, a staple forming plate is slidingly mounted in the housing along with biasing spring means cooperatively associated with the actuating handle.

The present invention also incorporates a unique support handle which slidingly engages and securely interlocks and interconnects with the housing. In addition to a secure interlocked engagement, the support handle provides for comfortable gripping of the surgical stapler of the present invention by all users, regardless of hand size.

Finally, the entire surgical stapling instrument of the present invention is completed by an actuating handle having a front portion slidingly engageable within the housing for controlled nested interconnection with the staple forming plate, and a pivot pin about which the actuating handle pivots.

The surgical stapling instrument of the present invention comprises a minimum of parts to achieve the desired surgical stapling instrument, while also attaining an easily handled and comfortable stapling instrument for use by all personnel, regardless of the varying grip requirements of the individuals. In addition, the surgical stapling instrument of the present invention attains completely controlled staple formation with all of the prior art difficulties virtually eliminated.

The invention accordingly comprises a product possessing the features, properties, and the relation of components which will be exemplified in the product hereinafter described, and the scope of the invention will be indicated in the claims.

THE DRAWINGS

For a fuller understanding of the nature and objects of the present invention, reference should be had to the following detailed description taken in connection with the accompanying drawings, in which.

BEST MODE FOR CARRYING OUT THE INVENTION

Figure 1:
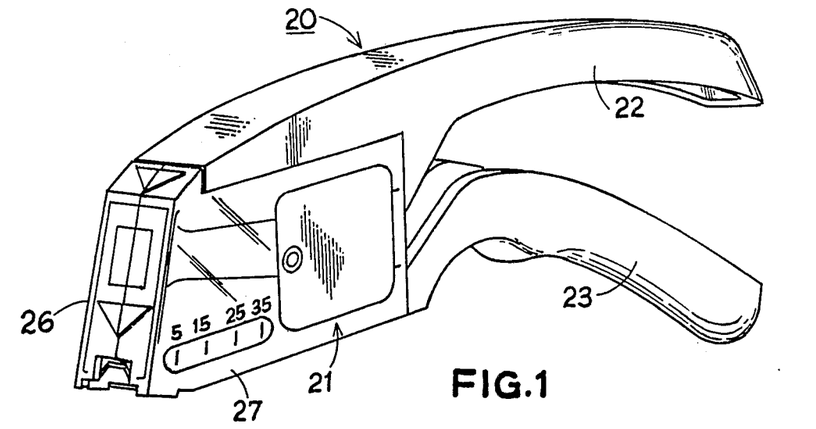
FIG. 1 is a perspective view showing the surgical stapling instrument or the present invention.

In FIG. 1, surgical stapling instrument 20 of the present invention is shown comprising a housing 21, a support handle 22, and an actuating handle 23. Housing 21 preferably comprises two matingly engageable half sections 26 and 27, which comprise substantial mirror images of each other and are constructed for secure, cooperating interconnected mounted interengagement to form housing 21. In this way, the desired rapid and easily attained assembly is achieved.

Figures 2, 3, 4, 5, 6, 7:
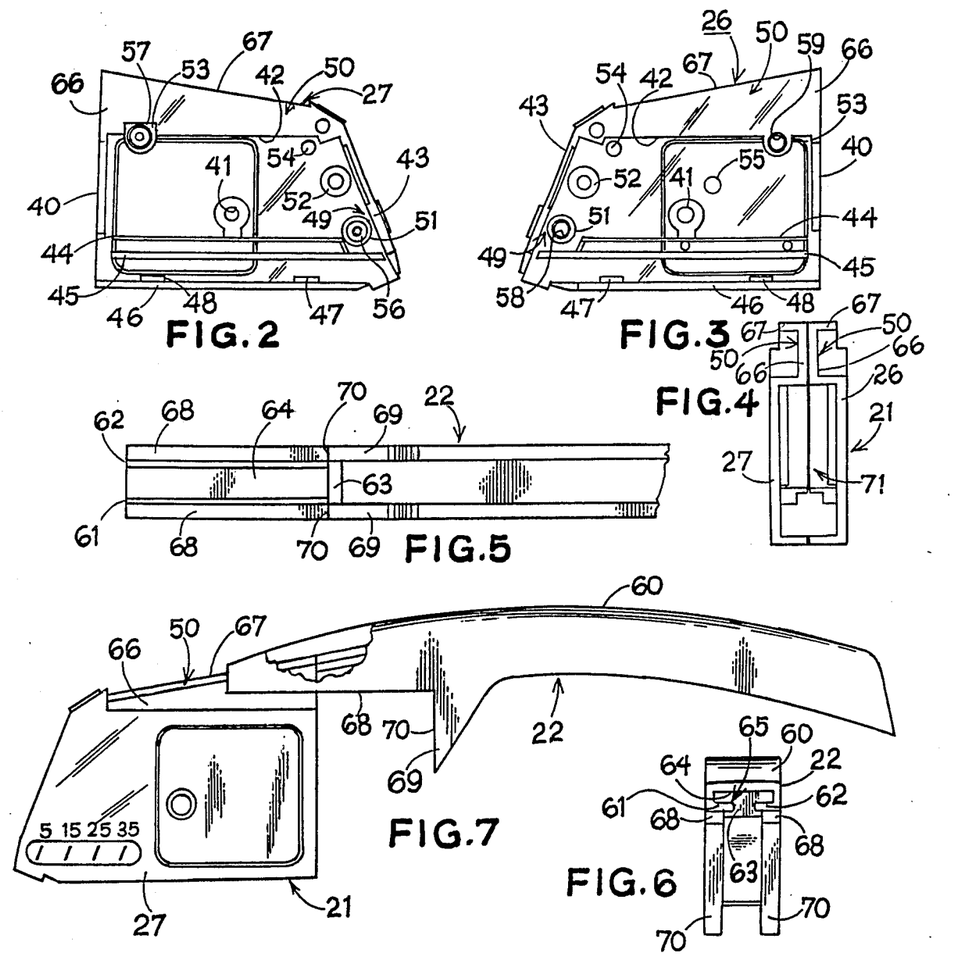
FIGS. 2 and 3 are both side elevation views showing the inside construction of the two housing portions forming the housing of the surgical stapling instrument of the present invention.
FIG. 4 is a rear elevation view showing the housing portions fully assembled.
FIG. 5 is a bottom view, partially broken away, of the support handle of the surgical stapling instrument of the present invention.
FIG. 6 is a front elevation view of the support handle of the surgical stapling instrument of the present invention.
FIG. 7 is a side elevation view showing the support handle in the process of being slidably, lockingly, interconnected with the fully assembled housing of the surgical stapling instrument of the present invention.

As shown in FIGS. 2 and 3, each of the housing sections 26 and 27 comprise a sidewall 40, an upper panel 42, a front panel 43, and a lower panel 46, with each of the panels extending substantially perpendicularly from wall 40. In addition, a pivot-pin supporting aperture 41 is formed in each sidewall 40. When housing sections 26 and 27 are in secure mounted interengagement, the two pivot-pin supporting apertures 41 are in cooperating, juxtaposed spaced aligned relationship with each other for retained supporting engagement of a pivot pin, while panels 42, 43 and 46 of section 26 are in abutting contact with panels 42, 43 and 46 of section 27, thereby attaining the substantially complete enclosure or housing 21.

Each of the inside surfaces of walls 40 of housing portions 26 and 27 incorporates an elongated handle supporting shelf 44 extending substantially perpendicularly from wall 40 below pivot-pin supporting aperture 41, substantially parallel to lower panel 46. Also, an elongated flange 45 extends substantially perpendicularly from wall 40 in juxtaposed, spaced, parallel alignment with elongated shelf 44 and lower panel 46.

Each housing section 26 and 27 also incorporate notches 47 and 48 formed in wall 40 directly above lower panel 46, and bosses 51, 52 and 53. Bosses 51 and 52 are aligned with front panel 43, defining therebetween a driver retaining passageway 49 which also extends to the zone between the forward terminating end of flange 45 and front panel 43.

Housing section 27 incorporates an alignment post 56 which extends from boss 51 and an alignment post 57 extending from boss 53. Housing section 26 incorporates a tapered post-receiving hole 58 formed in boss 51, and a tapered post-receiving hole 59 formed in boss 53. With this construction, housing sections 26 and 27 are quickly and easily securely mounted together by simultaneously aligning post 56 in hole 58 and post 57 in hole 59. Then, sections 26 and 27 are pushed into secure mated engagement, with posts 56 and 57 securely retained in holes 58 and 59.

In the preferred construction, housing sections 26 and 27 incorporate spring-retaining posts 54 extending from sidewall 40 for receiving one end of a biasing spring means. In addition, a post 55 extends from wall 40 of housing section 26 for positioning the opposed end of the spring means during assembly.

Finally, housing sections 26 and 27 each incorporate an upstanding, inverted, L-shaped flange 50 extending perpendicularly from upper panel 42. Preferably, each flange 50 comprises a substantially flat, upstanding plate 66 having a sloped terminating end, and a track-forming portion 67 extending perpendicularly from the sloped end of plate 66. As detailed below, flanges 50 of housing sections 26 and 27 are in abutting, cooperating engagement in assembled housing 21, to form a handle guiding and interlocking holding track.

One of the unique aspects of the present invention is the sliding, interlocking, interconnected engagement of support handle 22 with housing 21. By referring to FIGS. 4 through 7, along with the following detailed disclosure, this unique sliding, interlocking, secured interengagement can best be understood.

Upper handle 22 incorporates a smoothly curved top surface 60 which extends the entire length of handle member 22, and is shaped for being comfortably held in the palm of the user's hand. Handle 22 also incorporates a substantially flat, forwardly positioned bottom surface 64. At the proximal end of handle member 22, two longitudinally extending, elongated, juxtaposed, spaced, cooperating flanges 61 and 62 are mounted in spaced, parallel relationship to substantially flat bottom surface 64, with elongated flanges 61 and 62 terminating in abutting relationship with a vertically disposed rib member 63. As best seen in FIG. 6, an elongated channel 65 is formed between lower surface 64 and flanges 61 and 62.

Handle 22 also incorporates substantially flat housing engaging edges 68 on both sides thereof, with each of the substantially flat edges 68 terminating at elongated fin members 69. Each fin member 69 incorporates a forward, substantially flat surface 70 which extends from edge substantially perpendicularly from edge 68. In this way, a flat, right angularly shaped house-abutting configuration is attained, providing secure, mounted engagement with housing 21.

As best seen in FIGS. 4 and 7, housing 21 comprises a sloped, channel-engaging track, formed by L-shaped flanges 50—50 of housing sections 26 and 27. In the preferred embodiment, the channel-engaging track comprises a downwardly sloping surface when moving from the rear of housing 21 towards the front of housing 21. By employing the teaching of this invention, the proximal end of handle 22 with its elongated flanges 61 and 62 peripherally surrounding and interlocking with track forming portions 67—67 of flanges 50—50. Since track forming portions 67—67 slope downwardly, handle 22 advances in the same downward direction as handle 22 is moved to further locked, secure, interengagement with L-shaped flanges 50—50 of housing 21. Handle advancement continues until housing abutting surfaces 68 and 70 of handle 22 come into direct contact with housing 21. In this way, a positive, secure, interlocked and fully engaged surgical stapling instrument is attained in a quickly, easily assembled construction. In addition, the sloping track allows handle 22 to be raised upwardly during the assembly of actuating handle 23, thereby assuring added assembly ease of handle 23.

In addition, by constructing L-shaped flanges 50—50 with substantially track-forming portions 67—67 and constructing handle member 22 with a substantially flat inside surface 64, the surface of portions 67—67 are in direct contact with inside surface 64 of handle member 22. In addition, flanges 61 and 62 are in underlying abutting engagement with the opposed surface of portions 67—67. As a result, securely embraced, wobble-free, interengagement of handle member 22 with housing 21 is achieved.

By employing the teaching of the present invention, prior art difficulties and disadvantages of having a single housing-handle combination are totally eliminated. As a result, using the teaching of this invention, separate materials may be employed for housing 21 and handles 22 and 23. Also, alternate handle configurations can be interchangeably mounted to housing 21.

In the surgical stapler of the present invention, a transparent plastic material is preferably employed for housing 21, while handles 22 and 23 are formed from opaque plastic material. In this way, the user is capable of seeing the entire staple formation process through the transparent plastic material of housing 21, while handles 22 and 23 are readily discernible and identifiable, since they are formed from conventional opaque plastic material.

Figure 8:
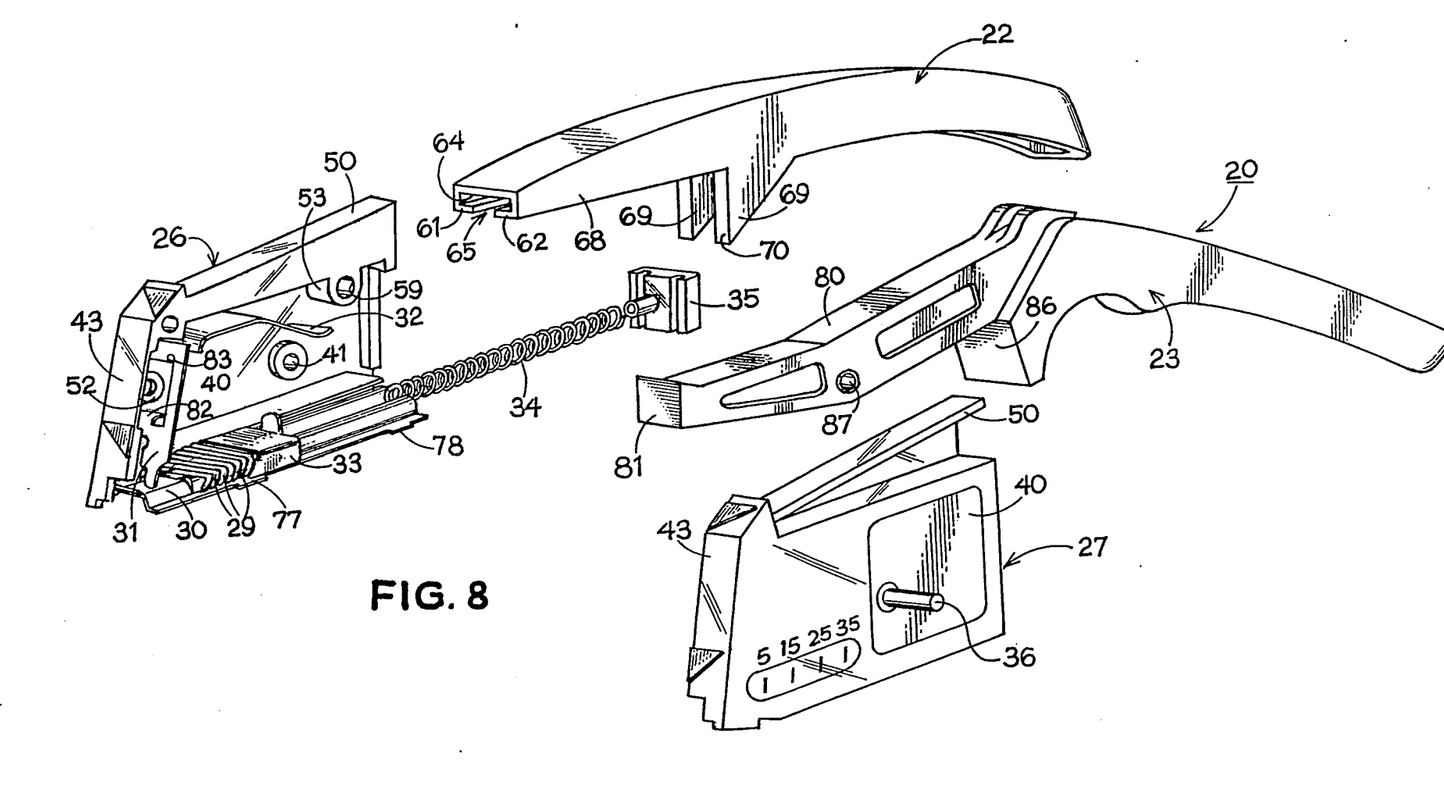
FIG. 8 is an exploded perspective view showing all of the components forming tne surgical stapling instrument of the present invention.

In FIG. 8, surgical stapling instrument 20 of the present invention is shown in an exploded perspective view, detailing all of the components employed in forming the easily constructed, readily assembled surgical instrument of the present invention. As detailed above, surgical stapler 20 of the present invention incorporates a housing 21 comprising housing sections 26 and 27, a support handle 22 which is slidably interengaged in secure, mounted, interlocking engagement with housing 21 and an actuating handle 23.

In addition, surgical stapling instrument 20 incorporates a staple supporting channel member 30, a movable staple forming plate 31, and a handle biasing spring 32. Also, staples 29, a staple pusher 33, which is slidingly engaged along staple supporting channel member 30, spring means 34, and a spring anchor 35 are included. Finally, a pivot pin 36 is employed to assure the desired pivoting movement or actuating handle 23. Using these components, the surgical stapling instrument of the present invention is completely attained.

As is readily apparent from this description, as well as the following detailed disclosure, the surgical stapling instrument 20 of this invention comprises a minimum of component parts which can be quickly and easily assembled in an efficient production line, thereby attaining a minimum of assembly cost while achieving a dependable surgical stapling instrument having consistent, repeatable effective results.

Figures 9, 10:
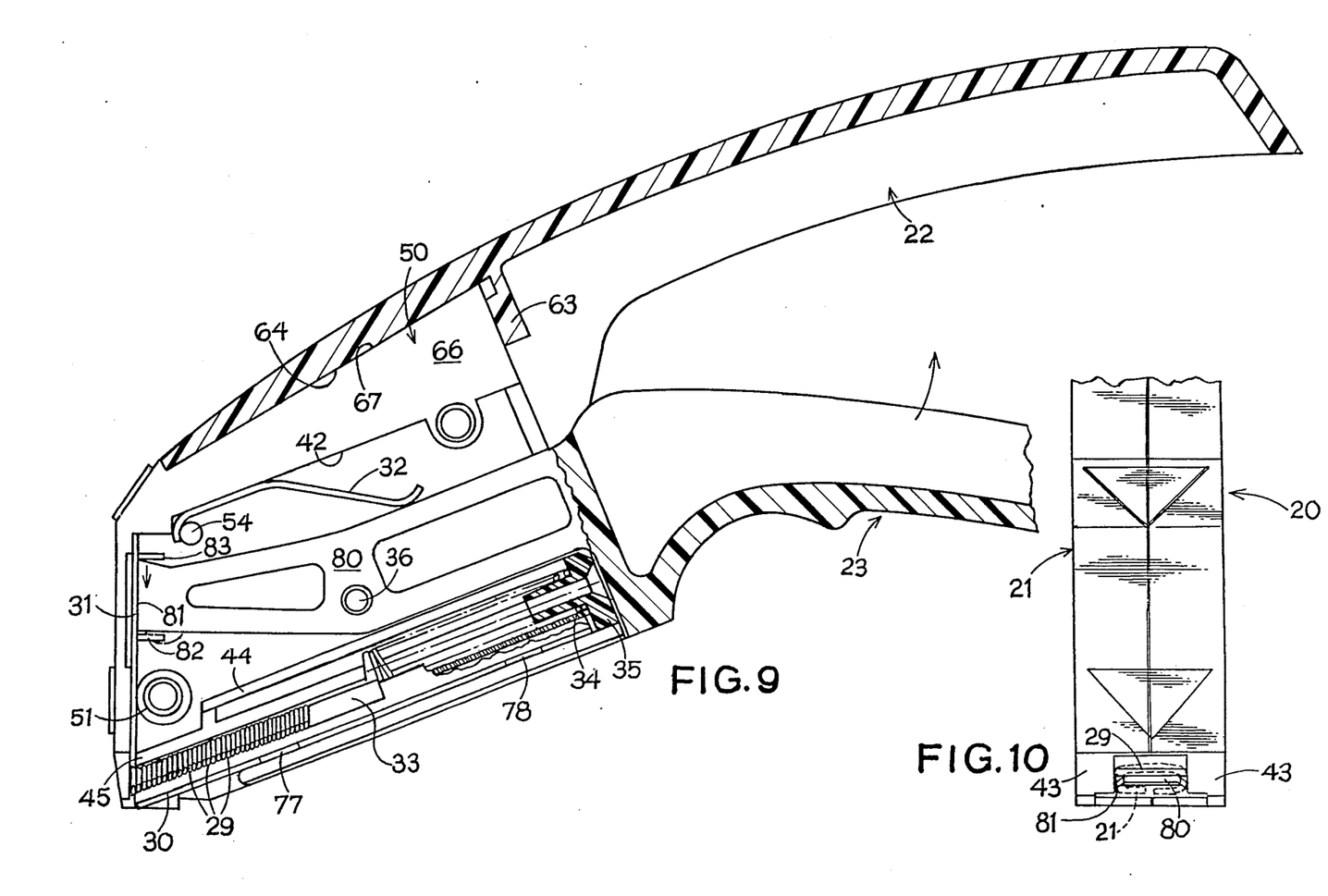
FIG. 9 is a side elevation view, partially in cross-section and partially broken away, showing the fully assembled surgical stapling instrument of the present invention.
FIG. 10 is a front elevation view of the surgical stapling instrument of the present invention.

By referring to FIGS. 8 and 9, the rapid, easily achieved assembly of surgical instrument 20 of the present invention can best be understood. As discussed above, the surgical stapler 20 of the present invention incorporates an independent, separately assembled housing 21. The assembly of housing 21 is initiated by first positioning staple supporting channel member 30 into housing section 26 by engaging position locating tabs 77 and 78 in recesses 47 and 48 of housing portion 26. Then staple forming plate 31 is mounted in passageway 49 of housing section 26, in abutting, sliding interengagement between front panel 43 and bosses 51 and 52. Handle biasing spring 32 is then mounted to housing section 26 by securing one end of spring 32 about retaining post 54, and placing the opposed end on top of pin 55.

Next, the sub-assembly of housing 21 is completed by securely, matingly engaging housing section 27 with housing section 26. This is achieved as described above, by inserting aligning/locking pins 56 and 57 of housing portion 27 within receiving apertures 58 and 59 of housing section 26. Once housing sections 26 and 27 are matingly, securely engaged with each other, they are permanently fastened to each other by sonic welding of all abutting edges.

The next step in the assembly process is the mounting of staples 29 on staple supporting channel member 30. Next, staple pusher/follower 33 is mounted in position behind the last staple 29, with biasing spring 34 positioned in channel member 30, with one end thereof in biasing engagement with staple pusher/follower 33. Then, spring anchor 35 is placed in engagement with the opposed end of biasing spring 34 and secured by tabs in abutting engagement with the rear surfaces of housing 21. In this way, the secure, complete, trouble-free assembly of housing 21 is achieved, along with the resulting efficacious operation.

With housing 21 fully assembled, the assembly of surgical stapling instrument 20 is quickly and easily completed by slidably interconnecting support handle 22 with L-shaped flanges 50 of housing 21 into the secure, interlocked, interengaged manner detailed above. Then, actuating handle 23 is inserted into entry zone 71 formed in the rear of housing 21 (shown in FIG. 4) with the forwardly extending finger portion of actuating handle 23 being slidably inserted between spring 32 and shelf 44. Typically, handle 22 is moved rearwardly along the sloped track formed by flanges 50—50, thereby causing handle 22 to be lifted upwardly relative to housing 21. This assures that sufficient clearance is provided for ease of insertion of actuating handle 23 into housing 21. When in its final position, forward plate-engaging tip 81 of finger 80 of handle 23 is in secure, retained driving engagement with staple forming plate 31, positioned between fins 86 and 83 of plate 31. In addition, substantially flat surface 86 of actuating handle 23 is in abutting contact with the rear surface of anchor 35. This position defines the unactuated, resting position of handle 23 with housing 21.

The assembly of surgical stapling instrument 20 is then completed by merely inserting pivot pin 36 into pin receiving hole 41 formed in housing section 27, and then advancing pin 36 through aperture 87 of actuating handle 23 until one end of pin 36 is inserted into pin supporting aperture 41 of housing section 26. Once pin 36 is fully inserted into housing 21, with handle 23 pivotally supported thereby, the assembly of surgical stapling instrument 20 is complete.

Once surgical stapling instrument 20 of the present invention has been fully assembled, instrument 20 preferably is sterilized and packaged ready for use in surgical stapling procedures. It has been found that the surgical stapling instrument 20 of this invention eliminates the prior art difficulties which have been encountered and attains a dependable, completely repeatable, efficient stapling instrument usable in all surgical stapling procedures. In addition, the surgical stapling instrument 20 of this invention, which is constructed for preferable disposable use, is easily employed and handled. By referring to FIGS. 9 and 10, the overall efficient and direct operation of the surgical instrument of this invention can best be understood.

In order to actuate surgical stapling instrument 20 of this invention and implant the surgical staple in the skin or fascia of the patient, a surgeon need only grasp surgical instrument 20 in his hands with support handle 22 firmly held in the palm of the hand, with the surgeon's fingers wrapped around actuating handle 23. Then, by merely squeezing handles 22 and 23 towards each other, actuating handle 23 pivots about pivot pin 36, causing plate engaged tip 81 of handle 23 to move downwardly, as shown in FIG. 9, which causes staple forming plate 31 to simultaneously move downwardly therewith. As is fully detailed below, the movement of staple forming plate 31 causes the first staple in the staple row to be formed about the staple forming platform 80 extending from staple supporting channel member 30.

Figure 15:
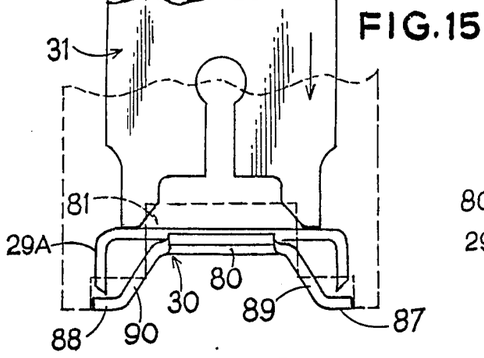
FIGS. 15, 17, 19 and 21 are successive front elevation views, partially broken away, showing successive stages of the staple forming process.
Figures 21, 22:
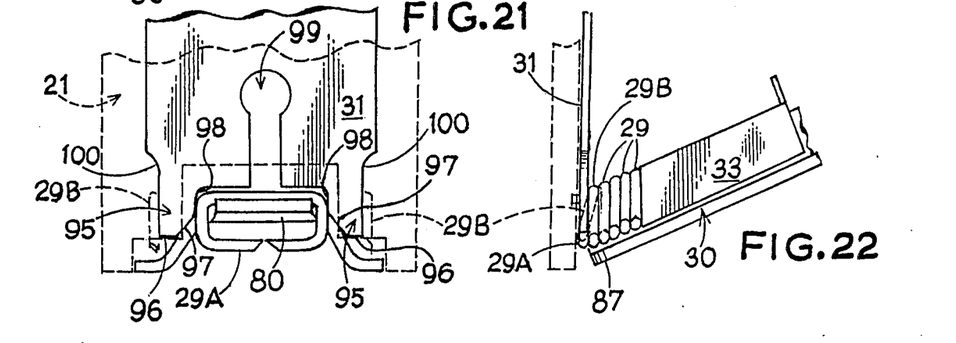

As best seen in FIGS. 10, 15 and 21, staples 29 are incapable of exiting from surgical stapling instrument 20 prior to formation, since the unformed staple can not exit through portal 81 of housing 21. Consequently, the unformed staples 29 are retained within housing 21, abutting front wall panels 43. However, as shown in phantom in FIG. 10, when staple 29 has been fully formed into its completed, substantially rectangular configuration, staple 29 easily exits through portal 81, for retained embedment in the fascia or skin of the patient.

With the surgical stapling instrument 20 of this invention, the surgeon is assured that a single staple 29 is formed each and every time handle 23 is actuated, without fear of jamming or unwanted staple movement, even if actuating handle 23 is released during the formation process. As discussed above, this is one of the principal difficulties found in prior art surgical stapling instruments.

In addition, the surgical stapling instrument of this invention achieves a positive release of the formed surgical staple 29 once the staple formation has been fully completed. This positive release is achieved by a combination of the staple being retained within housing 21 by front panels 43 until the staple has been fully formed for exiting through portal 81, in combination with the biasing forces of spring 34 and pusher/follower 33, advancing the row of staples 29 towards portal 81 while simultaneously pushing the formed staple through portal 81.

One of the principal unique aspects of surgical stapling instrument 20 of the present invention is the uniquely constructed staple supporting channel member 30. By referring to FIGS. 11 through 14, along with the following detailed disclosure, this unique channel member construction can best be understood, as well as the consistent, repeatable, jam-free staple operation attained therefrom.

As discussed above, one of the major drawbacks of prior art surgical staples is the inability of the prior art staples to prevent jamming as well as prevent staple movement or rotation prior to or during the formation process. In addition, staple jamming and staple movement is almost universally encountered in prior art surgical staples every time a non-locking actuating handle is released during the formation process. However, by employing the teaching of the present invention, undesirable staple jamming as well as staple rotation is virtually eliminated, without requiring the incorporation of a ratchet or other locking system for preventing the release of an actuated handle.

In tne surgical stapling instrument of the present invention these prior art difficulties and drawbacks are overcome by incorporating staple guiding and camming surfaces which cooperate with the staple during the entire formation process. In the preferred embodiment, the staple guiding and camming surfaces are formed in staple supporting channel member 30.

Figure 11:
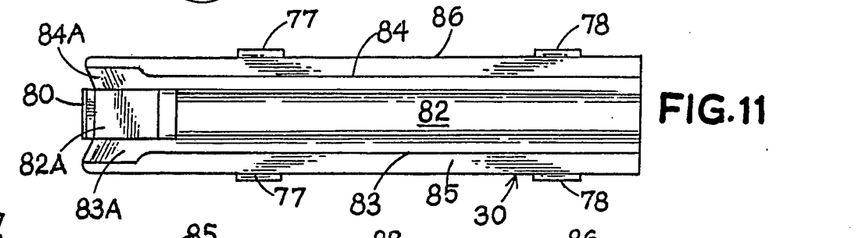
FIG. 11 is a top plan view of the staple supporting channel member incorporated in the surgical stapling instrument of the present invention.
Figure 12:
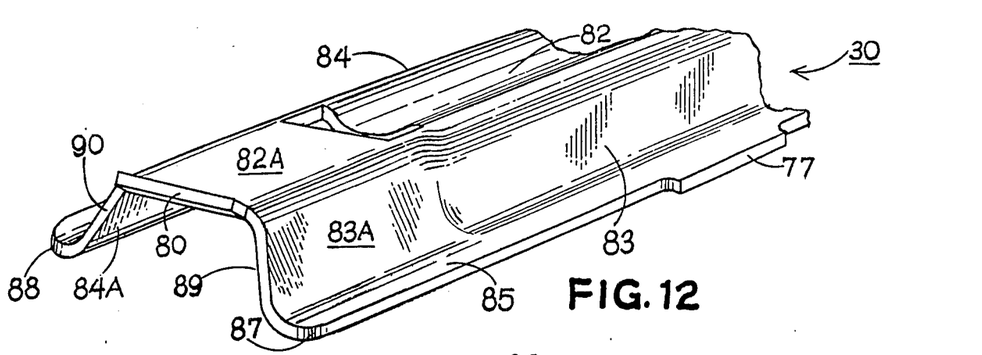
FIG. 12 is an enlarged, perspective view, partially broken away, of the staple supporting channel member incorporated in the surgical stapling instrument of the present invention.

As shown in FIGS. 11 and 12, staple supporting channel member 30 comprises an elongated, bridge portion 82 along which staples 29 (not shown) are slidably, supportingly mounted. In addition, staple supporting channel member 30 comprises elongated, substantially flat sidewalls 83 and 84 which extend substantially perpendicularly from bridge portion 82. Staple supporting channel member 30 also incorporates a side flange 85 which extends substantially perpendicularly from the terminating edge of sidewall 83 and a side flange 86 which extends substantially perpendicularly from sidewall 84. In the preferred embodiment, bridge portion 82 comprises a substantially concave shape extending substantially the entire length of bridge portion 82. In this way, a holding zone is formed for securely retaining spring means 34.

Figure 13:
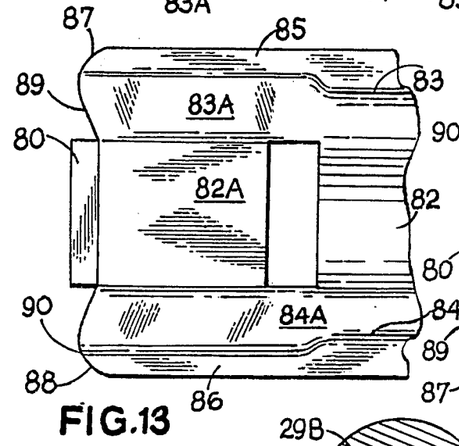
FIG. 13 is an enlarged bottom plan view, partially broken away, of the staple supporting channel member of the present invention, incorporated into the surgical stapling instrument of the present invention.
Figure 14:
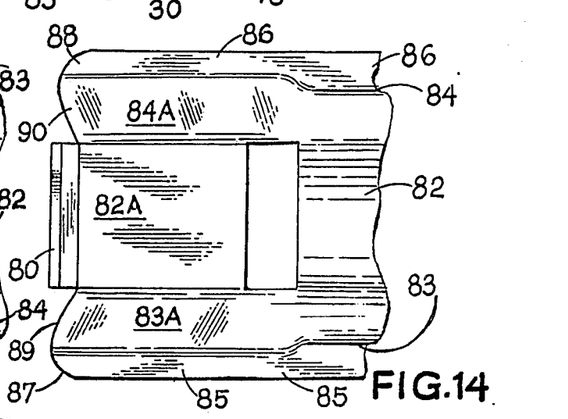
FIG. 14 is an enlarged top plan view, partially broken away, of the staple supporting channel member incorporated into the surgical stapling instrument of the present invention.

In general, the configuration of staple supporting channel member 30 described above represents the conventional construction for prior art staple supporting channel members. However, channel member 30 of the present invention has achieved a major advance over prior art surgical stapling instruments by discovering a unique staple cooperating configuration for the proximal end of staple supporting channel member 30. This unique and unobvious configuration is best seen in FIGS. 12 through 14.

In accordance with the teaching of the present invention, a forward section or proximal section of staple supporting channel member 30 comprises a unique construction not found in the prior art which achieves the desired staple control during the entire formation process, regardless of the speed of inconsistency in actuation pressure.

This staple formation control is achieved by providing staple supporting channel member 30 with depending sidewalls 83A and 84A which extend from staple supporting bridge portion 82A at a sloping, outwardly flaring angle therefrom. Although sloping sidewall 83A comprises an extension of sidewall 83, sidewall 83 is substantially perpendicular to bridge portion 82, while sidewall 83A is not perpendicular and, instead, angularly slopes away from bridge portion 82A. Similarly, sidewall 84A comprises an extension of perpendicular sidewall 84, but angularly slopes away from bridge portion 82A at an outwardly flaring angle.

Side flange 85 extends substantially perpendicularly from the terminating end of sidewall 83A, thereby comprising a continuous, substantially planar surface, the area of which is reduced adjacent sidewall 83A. Similarly, side flange 86 extends substantially perpendicularly from the terminating end of side wall 84A, providing a continuous, substantially planar surface having a reduced area adjacent sidewall 84A. In addition, the forward, proximal end of flange 85 terminats with a smoothly curved camming edge 87, while flange 86 terminates at its proximal end with a smoothly curved camming edge 88.

Similarly, sidewall 83A incorporates a staple guiding and camming edge 89 which is smoothly contoured and extends from a smoothly rounded and blended interconnection with terminating edge 87 of flange 85, and extends therefrom to staple forming platform 80. Similarly, side wall 84A terminates with a staple camming and guiding edge 90 which is smoothly contoured and extends from a smoothly rounded and blended interconnection with terminating edge 88 of flange 86, and extends therefrom to staple forming platform 80.

By incorporating staple camming and guiding edge surfaes 87, 88, 89 and 90 along with sloping sidewalls 83A and 84A, each and every staple positioned on staple forming platform 80 are controllably guided and cammingly advanced to assure that each and every staple is completely formed and is incapable of being moved or pivoted into undesirable positions. Furthermore, this construction prevents staple jamming or unwanted second staple formation if actuating pressure is released during the formation process, and then reapplied.

As best seen in FIGS. 13 and 14, staple camming and guiding edges 87 and 88 comprise smoothly, rounded, outwardly curved surfaces. This smoothly, rounded, curved edge construction is extremely important in the initial formation of the staple. By incorporating the smoothly rounded, camming edge surfaces 87 and 88, each and every staple resting on platform 80 prior to formation is assured of being divided into the desired aligned orientation for forming. In particularly, if a staple to be formed is positioned on staple forming platform 80 with the tips thereof slightly tilted rearwardly, these tips and the side surfaces of the staple will contact camming edge surfaces 87 and 88 and will be cammingly guided by the smoothly, rounded, surface thereof into the desired position.

In this way, any staple which is tilted out of the plane of formation formed by staple forming plate 31 will be automatically pivoted into the desired plane as an integral part of the staple formation process. Consequently, each and every staple placed upon the staple forming platform 80 is formed in the desired configuration, without fear of jamming or improper staple forming.

In FIGS. 16 through 22, successive views showing both the front and side of staple supporting channel member 30 in cooperation with staple forming plate 31 are presented, detailing the various stages through which staple 29 moves during the forming or clenching process. By referring to these figures, along with the following detailed discussion, the controlled, cammingly guided, wobble-free and jam-free staple formation attained by the present invention can best be understood.

Figure 16:
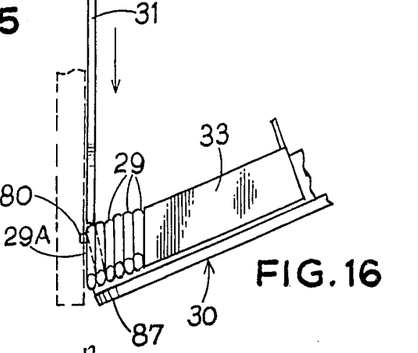
FIGS. 16, 18, 20 and 22 are corresponding successive side elevation views, partially broken away, showing the successive stages of the staple forming process.

In FIGS. 15 and 16, the staple to be formed, designated for convenience as staple 29A, is shown positioned on staple forming platform 80 prior to clenching, with staple forming plate 31 contacting staple 29.

Figure 17:
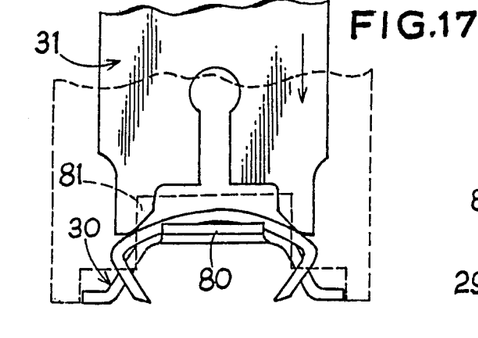
Figure 18:
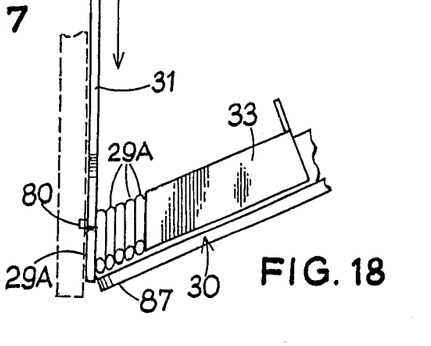

As actuation pressure on the handles of the surgical stapler of the present invention is applied, staple forming plate 31 advances downwardly, relative to staple supporting channel member 30, into contact with staple 29A, causing staple 29A to begin to bend about staple forming platform 80. As staple 29A moves from its initial position, as shown in FIGS. 15 and 16 to its partially formed position, as shown in FIGS. 17 and 18, staple 29A is brought into camming, guiding contact with cam surfaces 87, 88, 89 and 90.

Figure 19:
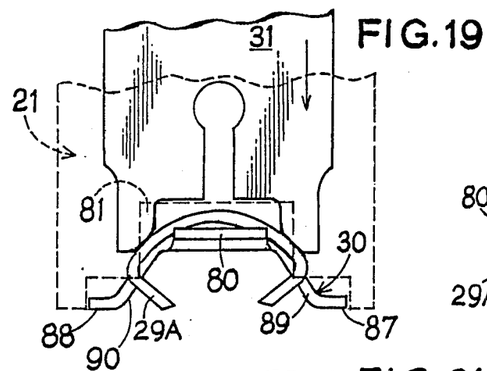

As detailed above, if staple 29A is improperly pitched with its tips extending rearwardly, as shown in phantom in FIG. 16, the tips and sides of staple 29A will initially contact camming and guiding edge surfaces 87 and 88. This sliding contact causes staple 29A to be controllably pivoted into the desired position, with the surface of staple 29A contacting guiding and holding edges 89 and 90, as shown in FIGS. 18 and 19.

In addition to cammingly guiding and controlling the movement of staple 29A during its initial formation, camming and guiding edge surfaces 89 and 90 of staple supporting channel member 30 provide guiding control and wobble-free support of staple 29A during its entire formation. In this way, when staple 29A is being formed into the desired configuration for embedment in the skin or fascia of the patient, supporting and guiding cam edge surfaces 89 and 90, in combination with front panel 43 of housing 21, prevent staple 29A from moving or wobbling into any undesired pitch or orientation. As a result, a dependable, repeatable, jam-free operation is achieved.

Figure 20:
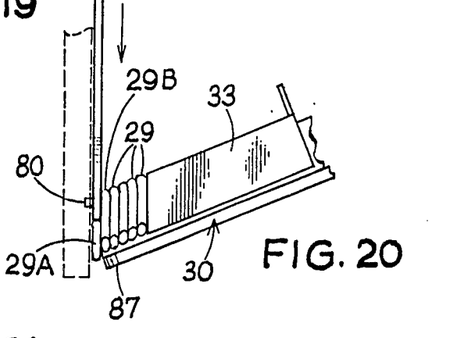

As the actuating force continues, staple forming plate 31 advances downwardly further, relative to staple supporting channel member 30, causing staple 29A to be increasingly bent about staple forming platform 80. As shown in FIGS. 19 and 20, staple 29A is continuously guided and cammingly advanced along edge surfaces 89 and 90 of staple supporting channel member 30 during the forming process, thereby preventing unwanted movement of staple 29A.

In addition, if the actuating force were removed, causing staple forming plate 31 to be drawn upwardly, out of contact with staple 29A, staple 29A remains in its partially formed position, without moving, pivoting, shifting or wobbling. In addition, the second staple in the row, designated for convenience as staple 29B, does not advance forwardly and, instead, remains in the same position as if staple forming plate 31 were in its staple contacting and forming position. Consequently, when actuating pressure is reapplied, staple forming plate 31 is moved downwardly into complete recapturing contact with the partially formed staple 29A, without contacting any other staple and without causing any double staple formation, jamming, or locking, typically encountered in prior art surgical staplers.

As the actuation pressure continues, staple forming plate 31 advances downwardly, further relative to staple supporting channel member 30, until staple 29A is completely formed, as shown in FIGS. 21 and 22. Once in this completely formed position, staple 29A is ready to exit through portal 81 of housing 21 as soon as the actuating forces are removed and staple forming plate 31 is moved out of contact with staple 29B, thereby allowing the spring forces acting on staples 29 and follower 33 to push staple 29A through portal 81 and advance staple 29B onto staple forming platform 80.

In FIGS. 16, 17, 19 and 22, housing 21 with its staple exit portal 81 is shown in phantom. In this way, it is readily seen that staple 29A is incapable of exiting from housing 21 until staple 29A has been completely formed, as shown in FIG. 22. As a result, staple movement or dislodgement prior to complete formation of staple 29A into the desired configuration is prevented and smooth, dependable operation is further enhanced.

Another feature incorporated into the surgical stapling instrument of the present invention is the staple contacting configuration of staple forming plate 31. As best seen in FIG. 21, staple forming plate 31 incorporates two staple forming fingers 95, each of which incorporate a leading edge 96, a side edge 98 lying in a plane substantially perpendicular to lead edge 96, and beveled edge 97 interconnecting edges 96 and 98. In addition, staple forming plate 31 incorporates a keyhole shaped relief zone 99 positioned between forming fingers 95.

In operation, it has been found that staple 29A can be controllably advanced into each and every partially formed position as staple 29A moves from complete contact with edge 96 to complete contact with beveled edge 97, as shown in FIGS. 15, 17 and 19. However, when staple 29A is in the position shown in FIG. 19, with staple 29A contacting the juncture between beveled edge 97 and side edge 98, staple forming plate 31 can no longer be controllably advanced. Instead, plate 31 moves quickly from the position shown in FIG. 19 to the fully staple-formed position shown in FIG. 21. In addition, the configuration of fingers 95 with its beveled edges 97 reduces the forces needed to form staple 29A, thereby further enhancing the usability of surgical stapling instrument 20.

As a result of this construction, the user is assured that staple 29A is incapable of being partially formed into a configuration which could allow staple 29A to exit through portal 81. Instead, the formation of staple 29A can be completely controlled and slowly achieved through all stages until staple 29A is almost ready to exit through portal 81 of housing 21. However, when fully clenched formation is imminent, staple forming plate 31 quickly advances downwardly, completely forming staple 29A into the desired configuration. As a result of this construction, the present invention attains repeatability and the prevention of jamming, staple locking, or embedment of partially formed staples.

Another feature incorporated into the surgical stapling instrument of the present invention is the incorporation of relieved side edges 100 on both sides of staple forming plate 31. By incorporating relieved side ecges 100, with the relief zone not employed for clearance of internal components, a staple tip entry zone is achieved, into which the tips of staple 29B are capable of advancing during the upward movement of staple forming plate 31 after the previous staple has been fully clenched and actuating force has been removed.

As shown in FIGS. 21 and 22 by the phantom drawing of staple 29B, the tips of staple 29B are capable of moving forwardly into the entry zone created by relieved side edges 100 of staple forming plate 31 before the crown portion of staple 29B is capable of being pushed onto staple forming platform 80. This forward movement of the tips of staple 29B occurs as soon as staple forming plate 31 moves upwardly, back towards its original unactuated position. This staple movement is caused by the inside surface of plate 31 frictionally contacting the crown portion of staple 29B, as plate 31 moves upwardly. This sliding contact causes staple 29B to pivot, with the tips thereof moving forwardly.

Consequently, by providing tip entry zones formed by relieved side edges 100, the tips of staple 29B are capable of entering this zone, thereby being present in the desired location, prior to having the crown of staple 29B forced onto platform 80. As a result, added assurance is provided that the staple resting on platform 80 is in the precise position required for complete trouble-free formation and embedment in the skin or fascia of the patient. In this way, repeatability of the surgical instrument of the present invention is further enhanced, while unwanted jamming is prevented.

Figure 23:
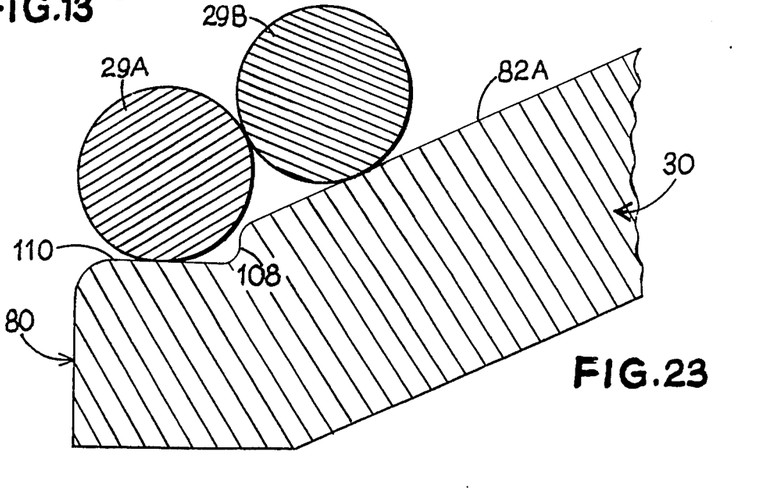
FIG. 23 is a cross-sectional side elevation view, partially broken away, showing an embodiment of the staple supporting channel member incorporated into the surgical stapling instrument of the present invention.

In FIG. 23, one embodiment which can be employed in the construction of staple supporting channel member 30 is depicted. In this embodiment, a step 108 is formed at the juncture between bridge portion 82A of staple supporting channel member 30 and staple holding surface 110 of staple forming platform 80. As a result, bridge portion 82A and staple holding surface 110 comprise discontinuous, non-coextensive surfaces. In the preferred embodiment, step 108 comprises a dimension substantially equal to between about ten percent and thirty percent of the staple diameter.

By incorporating step 108, it has been found that staple 29A, resting on surface 110 of staple forming platform 80, is more securely held in the desired forming position by the biasing forces exerted thereon by the second staple in the row, staple 29B, to a much greater extent than is found with prior art surgical stapling instruments. In addition, it is believed that staple 29B provides an added holding or locking action upon lead staple 29A. This is of particular assistance during transportation or vigorous movement ot the surgical stapling instrument.

In typical prior art surgical stapling instruments, wherein the staples are all aligned on a substantially planar or co-extensive surface, the staples are all tangent to each other with their central axes lying in substantially a single, identical plane. In addition, the spring biasing forces acting upon the staple row is applied through this common plane. However, by incorporating step 108 into the staple supporting channel member, the lead staple in the row, staple 29A, is held with its central axis below the plane defined by the central axis of staple 29B and all of the subsequent staples in the row.

Consequently, the forces acting upon the row of staples has its force transferred from staple 29B to staple 29A at a point above the central horizontal diametric plane of staple 29A. As a result, the usual rolling forces encountered by prior art surgical stapling instruments are avoided.

In addition, the crown portion of staple 29B abuttingly contacts the crown portion of staple 29A along a line higher than is conventionally found in prior art stapling instruments. As depicted in FIG. 23, this line of contact is above the tangent point of the central horizontal diametric plane of staple 29A. Consequently, staple 29B is capable of exerting a downward, holding force upon staple 29A, substantially eliminating possible dislodgement or movement of staple 29A which might otherwise occur during shipping or handling. Consequently, it is believed that by incorporating step 108 in staple supporting channel member 30 in order to provide a non-continuous or non-coextensive staple supporting surface thereon, staple securement is achieved which was heretofore unattainable. As a result, the jam-free, repeatable and dependable operation of the present invention is further enhanced.

It will thus be seen that the objects set forth above, among those made apparent from the preceding description, are efficiently attained and, since certain changes may be made in the above constructions, without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Having described our invention, what we claim as new and desire to secure by Letters Patent is:

1. A surgical stapling instrument comprising:
   A. a housing incorporating
      a. a staple supporting channel member mounted therein,
      b. a plurality of staples slidingly supported on the channel member for spring biased advancement therealong,
      c. a staple forming plate
         1. positioned for cooperative, forming engagement of the lead staple of the plurality of staples, and
         2. responsive to an actuation force for movement between a first, unactuated position and a second, staple engaging and forming position;
   B. an actuating handle
      a. pivotally connected to the housing, and
      b. drivingly engaged with the staple forming plate for controlled movement thereof in response to the application of an actuation force; and
   C. a support handle slidingly, interlockingly engaged with the housing for secured, mated, locked interconnection therewith,
   whereby separate materials can be employed for the housing and the handles while the entire assembly can be securely, interlockingly, matingly assembled quickly and easily.

2. The surgical stapling instrument defined in claim 1, wherein the housing comprises transparent plastic material and the handles comprise opaque plastic material, thereby providing the user with complete visibility of the entire forming process, while the handles possess a highly visible contrasting appearance.

3. The surgical stapling instrument defined in claim 1, wherein the support handle is further defined as comprising a track-engaging channel formed along the front end thereof and the housing further comprises:
   d. an upstanding track extending therefrom and positioned for cooperating, interlocking, interengagement with the track-engaging channel of the support handle, providing secure interconnected, interengagement therebetween.

4. The surgical stapling instrument defined in claim 3, wherein the support handle is further defined as comprising an elongated member having a substantially U-shaped cross-section throughout, and the track engaging channel is further defined as comprising:
   a. a substantially flat ceiling portion formed along the inside surface of the U-shaped handle member, and
   b. two elongated flange members extending inwardly from the sides of the U-shaped handle member in juxtaposed, spaced, parallel relationship with both of said flanges lying in substantially the same plane, with said plane being substantially parallel to the plane defined by the ceiling portion.

5. The surgical stapling instrument defined in claim 4, wherein said housing is further defined as comprising
   e. two mating, interconnecting portions, each of which comprises an upstanding, substantially L-shaped flange which cooperatingly abut to form the upstanding track.

6. The surgical stapling instrument defined in claim 5, wherein said upstanding, substantially L-shaped flange of each of said housing portions is forwardly, downwardly sloping thereby providing a forwardly, downwardly sloping track member whereby the sliding, interlocking, interengagement with said channel of said support handle establishes a downward interconnection of the support handle with the housing.

7. The surgical stapling instrument defined in claim 6, wherein the upstanding, downwardly sloping, track of said housing comprises an overall width less than the width of the housing, thereby providing a substantially continuous, substantially smooth surface between the abutting surfaces of the support handle and the housing.

8. The surgical stapling instrument defined in claim 1, wherein the actuating handle is further defined as comprising a single, elongated member, incorporating a longitudinally, forwardly extending finger, slidingly interengageable with the housing and controllably interconnected with the staple forming plate of said housing.

9. The surgical stapling instrument defined in claim 8, wherein the actuating handle is further defined as being spring biased for automatic positioning in its unactuated first position, when no forces are applied thereto.

10. A surgical stapling instrument comprising
    A. a housing incorporating
       a. a staple supporting channel member mounted therein, b. a plurality of staples slidingly supported on the channel member for spring biased advancement therealong, and
c. a staple forming plate
1. positioned for cooperative, forming engagement for the lead staple of the plurality of staples,
2. responsive to an actuation force from movement between a first, unactuated position and a second, staple engaging and forming position, and
3. defining a first, staple forming plane;
B. an actuating handle
a. pivotally connected to the housing, and
b. drivingly engaged with the staple forming plate for controlled movement thereof in response to the application of an actuation force;
C. a staple forming platform
a. positioned for receiving and supporting the lead staple of the plurality of staples as the staple forming plate engages said lead staple for forming the lead staple into the desired configuration for surgical use, and
b. defining a second plane positioned substantially perpendicularly to the first plane; and
D. guiding and supporting cam means
a. positioned below the staple forming platform adjacent at least both side edges thereof in juxtaposed, spaced cooperating relationship therewith,
b. defining a third plane positioned
1. substantially perpendicularly to the second plane formed by said platform, and
2. substantially parallel to the first plane formed by the staple forming plate, and
c. cooperatingly associated with the staple forming platform for controlled, supporting engagement of the lead staple during the forming process;
thereby assuring the lead staple is maintained in the desired position throughout the forming process, preventing unwanted movement of the staple, and substantially eliminating jamming double-staple actuation or formation.

11. The surgical stapling instrument defined in claim 10, further comprising
E. staple tip movement-control means positioned below the staple forming platform directly adjacent the staple tips and aligned for cooperative, camming control of the staple tips during the initial stages of formation of the lead staple, for controllably repositioning the lead staple into the desired plane of formation, assuring trouble-free staple formation, without unwanted jamming.

12. The surgical stapling instrument defined in claim 11, wherein the guiding and supporting cam means and the staple tip-movement control means are formed on the staple supporting channel member, rearwardly of the staple forming platform.

13. The surgical stapling instrument defined in claim 12, wherein the staple supporting channel member is further defined as comprising
1. an elongated staple supporting surface,
2. downwardly depending sides extending from said staple supporting surface on opposite side edges thereof,
3. outwardly extending flanges extending from the terminating edges of said downwardly depending sides,
4. guiding and supporting cam means formed along the forward terminating edges of said downwardly depending sides, and
5. staple tip-movement control means formed along the forward terminating edges of said outwardly extending flanges.

14. The surgical stapling instrument defined in claim 12, wherein at least the forward portion of the staple supporting channel member comprises
1. a substantially flat staple supporting surface,
2. two outwardly disposed, angularly flared side surfaces extending from opposed edges of said substantially flat staple supporting surface,
3. flange portions extending from the terminating edges of each of the side surfaces,
4. guiding and supporting cam means formed along the forwardly positioned terminating edges of said side surfaces, and
5. staple tip-movement control means formed along the terminating edges of said flanges.

15. The surgical stapling instrument defined in claim 14, wherein the guiding and supporting cam means and the staple tip movement control means are further defined as being formed along adjacent edge surfaces in a smoothly contoured curved surface with both of said means being in smoothly blended, cooperating, adjacent interconnection, thereby providing a substantially continuous smooth stapling controlling camming surface.

16. The surgical stapling instrument defined in claim 15, wherein said staple forming plate further comprises cut-out zones along the side edges thereof, adjacent the elongted staple forming fingers, thereby providing staple tip entry zones into which the second staple in the row can enter prior to the release of the previously formed staple.

17. The surgical stapling instrument defined in claim 14, wherein said staple supporting channel member is further defined as being positioned in juxtaposed, spaced cooperating relationship with a forward panel of the housing, with the housing incorporating a staple exit portal dimensioned to prevent unformed staples from exiting therethrough, while allowing fully formed staples to freely exit therethrough.

18. The surgical stapling instrument defined in claim 14, wherein said staple forming platform is further defined as being mounted to the staple supporting channel member, extending from the substantially flat staple supporting surface thereof, with the guiding and supporting cam means of the side surfaces of the staple supporting channel member being positioned in juxtaposed, staple controlling, cooperation therewith.

19. The surgical stapling instrument defined in claim 18, wherein said staple supporting channel member is further defined as incorporating a step zone positioned along the junction between said staple forming platform and said substantially flat staple supporting surface of said staple supporting channel member.

20. The surgical stapling instrument defined in claim 19, wherein said step zone is further defined as comprising an overall dimension of between about ten percent and thirty percent of the staple diameter.

21. The surgical stapling instrument defined in claim 10, wherein said staple forming plate further comprises:
3. staple forming fingers extending therefrom with said fingers comprising
 i. substantially flat rectangular shaped members,
 ii. each of said fingers having the inwardly, facing corner thereof beveled for reduced forming force and additional staple contact during the forming process.

22. A surgical stapling instrument comprising:
A. a housing incorporating
  a. a staple supporting channel member mounted therein,
  b. a plurality of staples slidingly supported on the channel member for spring biased advancement therealong,
  c. a staple forming plate
    1. positioned for cooperative, forming engagement of the lead staple of the plurality of staples,
    2. responsive to an actuation force for movement between a first, unactuated position and a second, staple engaging and forming position, and
    3. defining a first, staple forming plane, and
  d. an upstanding track extending therefrom positioned for cooperating, interlocking interengagement with a track-engaging channel found in the support handle;
B. an actuating handle
  a. pivotally connected to the housing, and
  b. drivingly engaged with the staple forming plate for controlled movement thereof in response to the application of an actuation force;
C. a support handle slidingly, interlockingly engaged with the housing for secured, mated, locked interconnection therewith, comprising
  a. an elongated member having a substantially U-shaped cross-section throughout, and
  b. a track-engaging channel formed along the front end thereof and comprising
    1. a substantially flat ceiling portion formed along the inside surface of the U-shaped handle member, and
    2. two elongated flange members extending inwardly from the sides of the U-shaped handle member in juxtaposed, spaced, parallel relationship with both of said flanges lying in substantially the same plane, with said plane being substantially parallel to the plane defined by the ceiling portion;
    c. cooperatingly associated with the staple forming platform for controlled, supporting engagement of the lead staple during the forming process;
D. a staple forming platform
  a. positioned for receiving and supporting the lead staple of the plurality of staples as the staple forming plate engages said lead staple for forming the lead staple into the desired configuration for surgical use,
  b. defining a second plane positioned substantially perpendicularly to the first plane;
E. guiding and supporting cam means
  a. positioned below the staple forming platform adjacent at least both side edges thereof in juxtaposed, spaced cooperating relationship therewith,
  b. defining a third plane positioned
    1. substantially perpendicularly to the second plane formed by said platform, and
    2. substantially parallel to the first plane formed by the staple forming plate, and
  c. cooperatively associated with the staple forming platform for controlled, supporting engagement of the lead staple during the forming process; and
F. staple tip movement-control means positioned below the staple forming platform directly adjacent the staple tips and aligned for cooperative, camming control of the staple tips during the initial stages of formation of the lead staple, for controllably repositioning the lead staple into the desired plane of formation, assuring trouble-free staple formation, without unwanted jamming.

* * * * *